US012664735B2

(12) United States Patent
Cagan et al.

(10) Patent No.: US 12,664,735 B2
(45) Date of Patent: Jun. 23, 2026

(54) MIXED REALITY COMBINATION SYSTEM

(71) Applicant: CARNEGIE MELLON UNIVERSITY, Pittsburgh, PA (US)

(72) Inventors: Jonathan Cagan, Pittsburgh, PA (US); Philip Leduc, Pittsburgh, PA (US); Ernest Kabuye, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 167 days.

(21) Appl. No.: 18/284,674

(22) PCT Filed: Apr. 18, 2022

(86) PCT No.: PCT/US2022/025212
§ 371 (c)(1),
(2) Date: Sep. 28, 2023

(87) PCT Pub. No.: WO2022/225847
PCT Pub. Date: Oct. 27, 2022

(65) Prior Publication Data
US 2024/0177427 A1      May 30, 2024

Related U.S. Application Data

(60) Provisional application No. 63/309,021, filed on Feb. 11, 2022, provisional application No. 63/176,637, filed on Apr. 19, 2021.

(51) Int. Cl.
*G06T 19/00* (2011.01)
*A61B 34/10* (2016.01)
*G02B 27/01* (2006.01)
*G06F 30/23* (2020.01)
*G06V 10/10* (2022.01)
*G06V 40/20* (2022.01)

(52) U.S. Cl.
CPC ............ *G06T 19/006* (2013.01); *A61B 34/10* (2016.02); *G02B 27/0172* (2013.01); *G06F 30/23* (2020.01); *G06V 10/16* (2022.01); *G06V 40/20* (2022.01)

(58) Field of Classification Search
CPC .......... G06F 3/011; G06F 3/017; G06F 3/013; G06T 19/006; G06T 2210/41; A61B 34/10; A61B 34/20; A61B 2090/365; A61B 2034/2055; A61B 34/25; A61B 90/37; A61B 2034/2065; A61B 2034/102; A61B 2034/104; G02B 27/017; G02B 27/0172; G02B 2027/0138; G06V 20/20; G16H 50/50
See application file for complete search history.

(56) References Cited

U.S. PATENT DOCUMENTS

2020/0053335 A1*   2/2020  Casas ..................... G06F 3/011

* cited by examiner

*Primary Examiner* — Farhan Mahmud
(74) *Attorney, Agent, or Firm* — KDW FIRM PLLC

(57) ABSTRACT

Disclosed herein is a system providing a mixed reality combination system that pairs augmented reality technology and an inertial measurement unit sensor with 3D printed objects such that user motions tracked by the inertial measurement unit as the user interacts with the 3D printed object is reflected in a virtual environment display of dynamic 3D imagery and augmented reality imagery.

25 Claims, 9 Drawing Sheets

MIXED REALITY COMBINATION SYSTEM

RELATED APPLICATIONS

This application is a national phase filing under 35 U.S.C. § 371 claiming the benefit of and priority to International Patent Application No. PCT/US2022/025212, filed Apr. 18, 2022, entitled "Mixed Reality Combination System", which claims the benefit of U.S. Provisional Patent Applications Nos. 63/176,637, filed Apr. 19, 2021, and 63/309,021, file Feb. 11, 2022, the contents of which are incorporated herein in their entireties.

GOVERNMENT INTEREST

This indentation was made with U.S. Government support under contract N000141712566 awarded by the Office of Navel Research, The U.S. Government has certain rights in the invention.

BACKGROUND

Task planning is a major facet of numerous fields such as healthcare, construction, and transportation because it allows for greater accuracy and speed in completing important tasks. To increase the performance of task planning approaches, systems that can mimic the potential environment with both computational and physical approaches can provide significant assistance to the user in performance of the task. A task planning system that is comprised of singular components acting in unison towards a common goal, is wholly functional if it can effectively execute a defined pre-planned task set by a user.

In the healthcare field, successful surgical procedures are characterized by the preplanning of routines to be executed during actual procedures. To achieve this, surgeons currently rely on a combination of the experience acquired from a combination of the use of cadavers, enabling technologies like virtual reality (VR) and their clinical years of practice to fully achieve positive surgical outcomes. However, cadavers lack dynamism and realism as they not only lack blood but also exhibit limited tissue deformation due to degradation and shrinkage. Further, current VR systems fail to provide amplified haptic feedback. These issues can affect the surgical training and thus increase the likelihood of medical errors during surgical procedural operations.

In the current medical space for task planning, physicians use visual planning tools like scanned images from computed tomography (CT) to guide them through a surgical procedure. In addition, the use of detailed simulated anatomical environments has also been pursued as this approach provides added benefits for surgical navigation. However, creating accurate physical environments that are unique can be resource-intensive due to the variations in physiology from person to person. In surgery, this approach is impractical as the models need to be both physically and visually realistic across a diversity of people. Furthermore, as previously mentioned, the use of cadavers as alternates for physically realistic models is challenging as they may not only fail to represent the anatomical physiology for specific procedures but are also not widely commercially available for unlimited use. To this end, surgeons rely heavily on their years of clinical exposure which can restrict challenging surgical procedures to a few specialists.

The use of virtual imagery in surgery through immersive engagement in systems, such as VR platforms for planning, has been shown to be effective in surgical operations such as those involving ortho-organic, traumatic, and microsurgery of the craniofacial skeleton. The current use of virtual imagery also provides opportunities for surgical technique iteration and examination in various clinical scenario settings as the surgical scene can be reused. In these instances, task planning using augmented reality (AR) systems have been based on three main areas: haptic feedback, sensitivity, and navigation. These areas make the approach comparable to industry standard VR systems/simulators that already employ these features.

FIG. 1 is a functional block diagram showing the current benchmark features of commercial VR systems that are used in task path planning. These properties represent the three main features that AR systems will also need to exhibit to adequately replace VR systems as the primary systems for task path planning.

The primary feature, referred to as haptic feedback, is the information response that virtual environments provide to the user based on the user's input or interaction. The information response can be characterized as a mix of sensory and force stimulation before, during, and after the user engagement with the target virtual platform and/or virtual object. Despite recent advances with realism in virtual environments, such as the use of 360° stereoscopic videos to enhance three-dimensional interaction, faulty estimates in egocentric distances between the human observer and surrounding objects still exist. These egocentric distances not only influence user interaction through poor depth perception but also tend to limit the ability of a VR system to be effective in task execution as they are negatively perceived. This negative perception of the haptic feedback due to misalignment further limits the realism associated with objects as they are deemed non-responsive, rendering VR systems inaccurate, and unreliable.

Efforts to combat this non-responsiveness include introducing haptic devices that are worn by the user to physically notify them of object interference during task execution or attaching hand-held force magnifiers on surgical tools. Unfortunately, these add weight to the tools, as they can be bulky and can also require advanced skill application among users to ensure task completion, thereby eliminating those with limited skills. Furthermore, the additional cost associated with using VR systems to provide these capabilities limits widespread integration into the medical and clinical practice.

The second feature, sensitivity, is the ability of the system to account for and quantify changes within its immediate virtual environment. This directly correlates with the alignment of the virtual imagery projected onto a target object and parameters associated with the user interaction (e.g., time to recognize the discrepancy or hesitancy to proceed due to image misalignment). Any misalignment that is expressed within the VR system can result in an incorrect pathology diagnosis. Thus, sensitivity is important because any minute difference in sensitivity can make a system unreliable and unusable.

The third feature of VR simulators, navigation, is the ability of the system to track the user and/or target object in a defined space to provide a feedback loop for image placement in the user's field of view. Objects that move dynamically can have multiple coordinates as they shift in real time. To obtain accurate measurements of these dynamic objects in scenarios involving virtual imagery, a combination of IMU sensors and optical trackers have been proposed. However, these optical trackers still require direct line of sight between the user and the target object, which can negatively impact surgical technique. IMUs can track object motion without the need to physically see the device, which can be a significant advantage.

Aside from the three features of VR systems that are needed to render them useful that have been highlighted above, additional issues exist. For example, inaccurate user hand-eye coordination while attempting to match virtual planning aids, can lead to difficulty in task planning execution. This difficulty in task planning execution is further exacerbated by the skill set of the user, which can range from novice to expert.

SUMMARY

Disclosed herein is a system and method for providing a novel Mixed Reality Combination System (MRCS) that pairs AR technology and an inertial measurement unit (IMU) sensor with 3D-printed, collagen-based specimens which the user interacts with. The system enhances a user's ability to accurately and effectively complete various tasks, for example, surgical procedures. As such, the invention will be explained in the context of a surgical procedure, however, it should be realized that the invention can be applied to many different fields, such as construction, maintenance and education.

In the context of a surgical procedure. MRCS charts a path prior to a surgical technique task execution for a user based on a visual, physical and dynamic environment on the state of a target object. To recreate environments in the form of augmented reality that can change different object states after user interaction, MRCS utilizes surgeon-created virtual imagery, that is projected onto a 3D-printed object (e.g., a bio-specimen), that reacts visually to user input on its real physical state. The user actions are then tracked using an inertial measurement unit (IMU) integrated with the system to not only determine the depth of the user's cuts into the 3D printed bio-specimen, but also to mark task execution. The combination of these multiple systems allows MRCS to react to the user in real time by displaying new multi-sensorial virtual states of an object prior to performing the task on the actual physical state of that same object, thereby enabling effective task planning.

BRIEF DESCRIPTION OF THE DRAWINGS

By way of example, a specific exemplary embodiment of the disclosed system and method will now be described, with reference to the accompanying drawings, in which:

FIG. 5 is a block diagram showing the finite element analysis process to create dynamic 3D imagery.

DETAILED DESCRIPTION

Given the identified limitations with current VR systems discussed in the Background section above, and to bridge these gaps, disclosed herein is an augmented reality (AR) system which is supplemented with user interaction with a physical 3D printed model of an object. This novel paradigm is referred to herein as a Mixed Reality Combination System (MRCS) 200, shown in block diagram form in FIG. 2.

AR is an approach that is related to the Reality-Virtuality (RV) continuum, which distinguishes objects from a real or virtual perspective. When a virtual object is brought into the physical environment, it is then referred to as AR. When a user interacts with an AR image or virtual environments in a physical space, then it is referred to as Mixed Reality (MR). These virtual environments are comprised of singular components that are generated and programmed to respond to user interactions either as a collective or within their singular pieces all in a module.

User interactions are defined as reciprocal actions or influence of the user with the objects in their physical and virtual environment. Once the virtual environments are placed via projection or via any other means onto any independent target. (i.e., an object outside the AR system), that target then exhibits dynamic motion independent of the virtual imagery. Then, the components within these virtual environments can either match these dynamic motions or demonstrate a dynamic path for the independent target based on user interactions.

The disclosed invention uses the field-of-view of the user to predict the future state of the target and then projects this predicted state in the form of an AR image into the field-of-space, enabling the user to visualize their intended action on the independent target.

The invention uses a combination of an AR environment and 3D printed objects to enhance task planning. This approach is important as it provides the required tactile, haptic feedback that would come from a user/object interaction through MR. Further, for surgical planning, where the anatomy is both unique in texture and size. 3D bio-printing of complete anatomical structures using collagen is employed. Such a system will look and feel more realistic to the user, and by inserting an IMU on a surgical tool, the precise incision or other procedure can not only be felt but also visually simulated.

This combination, when integrated into a single MR system architecture, provides avenues for task planning by not only incorporating realistic haptic feedback but also replicating complex anatomical pathologies. These are critical for surgical technique planning to reduce the lengthy clinical exposure time in training that is required for positive and efficient surgical execution. Using the invention, efficiency in task execution is improved using enabling technologies like AR, combined with physical 3D printed objects to pre-plan task execution.

Figure 1:
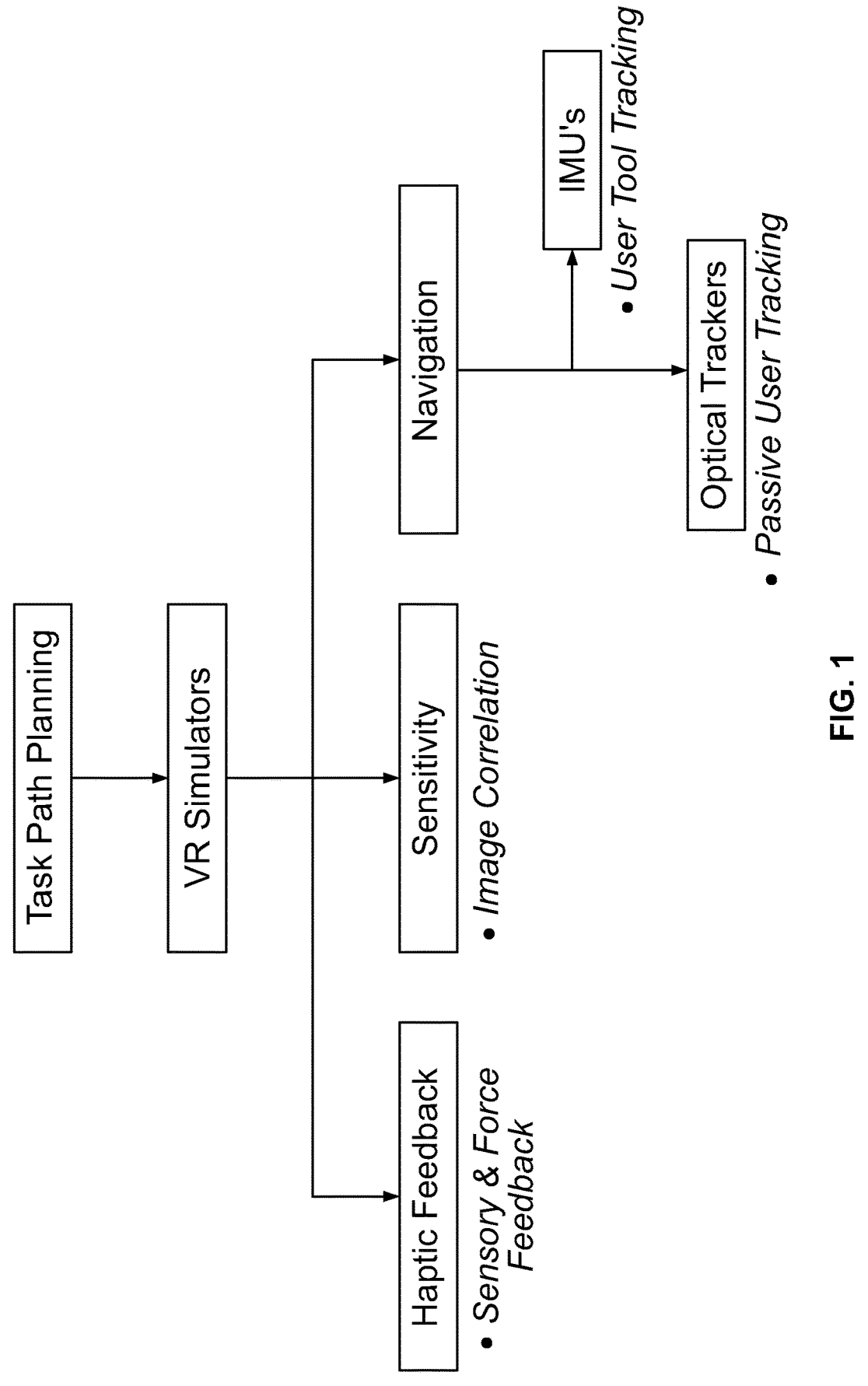
FIG. 1 is a block diagram showing feature properties of commercially available VR systems that are required for AR systems to adequately replace VR systems.
Figure 2:
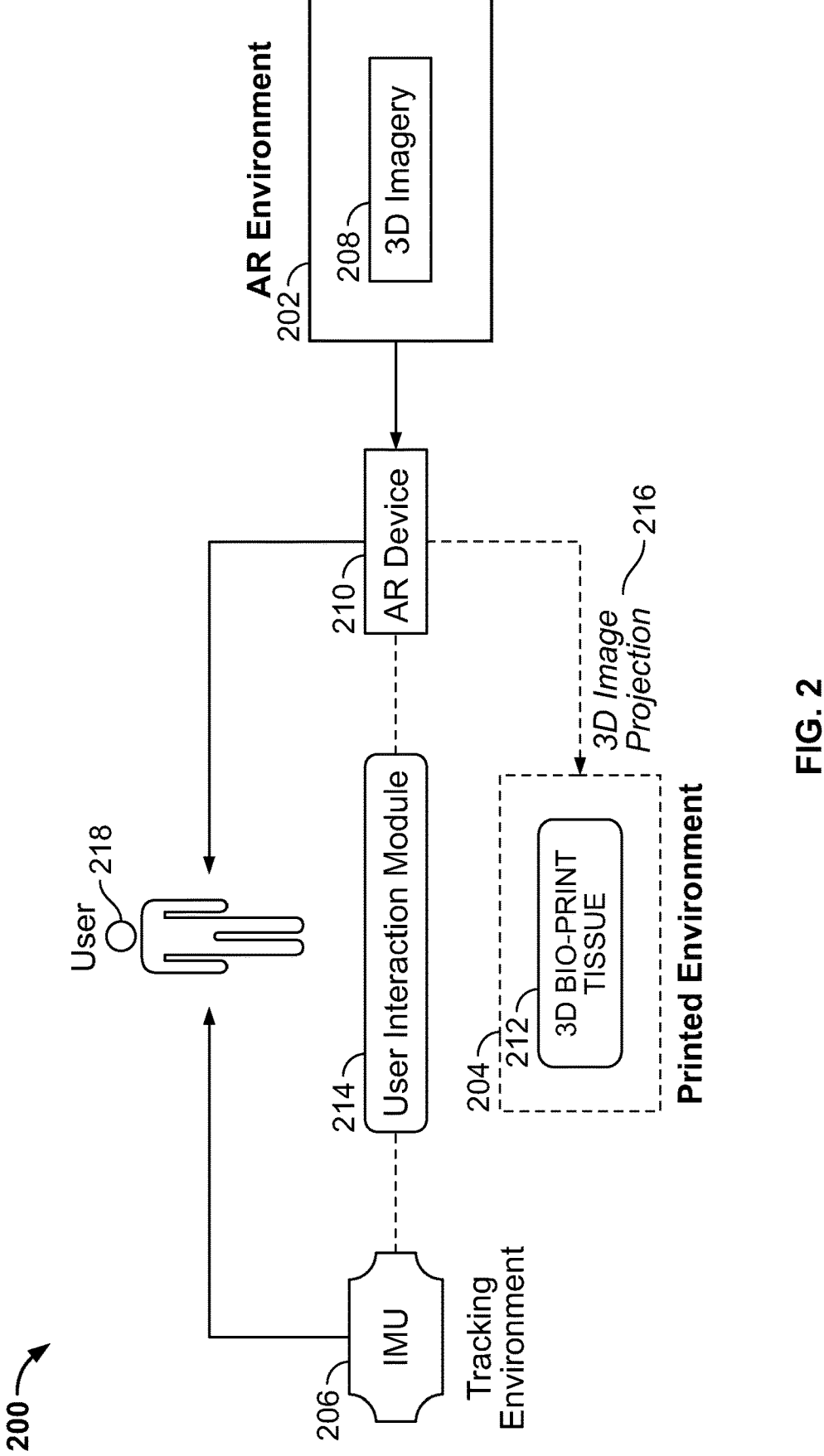
FIG. 2 is a block diagram showing the three main components (AR environment, printed environment and tracking environment) of the mixed reality combination system disclosed herein.

The MRCS 200 disclosed herein is shown in block diagram form in FIG. 2 and has three main components: the AR environment 202, the printed environment 204 and the tracking environment 206. AR environment 202 contains the composite virtual imagery 208 to be projected onto the target area. The AR Device 210 serves as the conduit platform through which AR environment 202 is placed in the user field-of-view, encompassing the target area and the dynamic target object which includes the 3D printed objects (e.g., a 3D printed bio-specimen). The user platform consists of the user interface interaction module 214 that houses the task planning schematic for any given task, the dynamic target on which the AR environment 202 is projected 216. The tracking system consists of the user tracking system 206 that relays user task location information, and the user 218 as the intended recipient of the task planning.

The three environments work together to project imagery 216 that guides and informs user 218 in planning a task for successful execution. The overall effect of the disclosed invention is that a user utilizing MRCS 200 is able to not only see projected 3D imagery 216 onto the 3D printed object 212 in their field-of-view, but also can interact with the 3D imagery 216 projected on object 212 dynamically. The 3D printed object 212 adds the realism expected from this interaction via haptic feedback through the 3D printed object 212, as the projected imagery 216 adapts and guides user 218 through the steps of the procedure.

AR Environment—The augmented reality environment 202 consists of the 3D models, finite element analysis (FEA) modeling and the virtual environment.

Figures 3A, 3B, 3C:
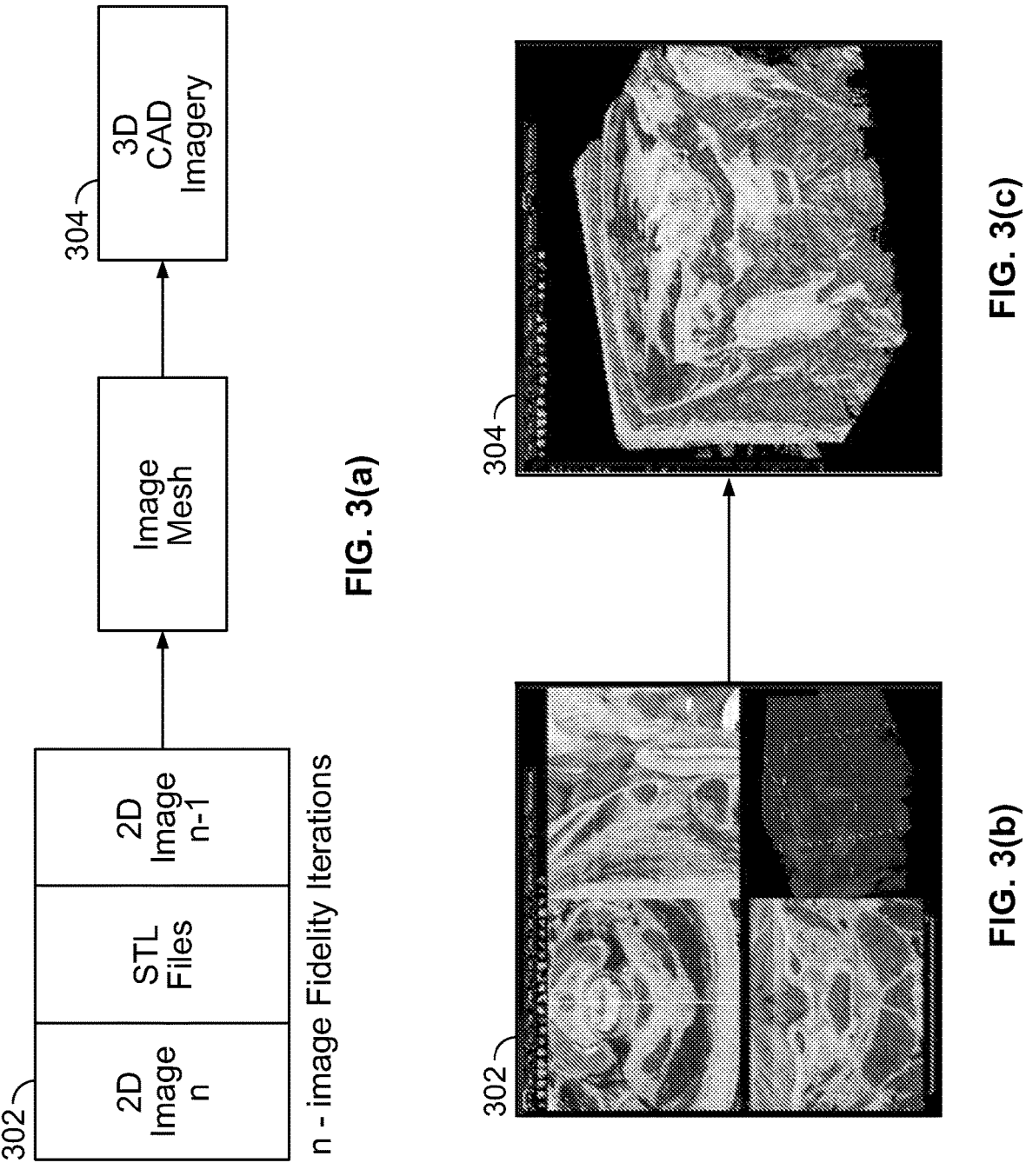
FIG. 3(a) shows the 2D image stitching process in which multiple 2D images, shown in FIG. 3(b) are stitched together to create a 3D CAD Imagery, shown in FIG. 3(c) using the stereolithography (STL) files of the 2D images.

Virtual environments can be created using 3D models of actual objects. To accomplish this, AR imagery is first obtained by stitching together multiple 2D images to create detailed composite models with the required level of object fidelity for printing. This process is shown in FIG. 3(a). Stitching involves integrating multiple layers of images 302, shown in FIG. 3(b), for an object to create a singular 3D image 304, shown in FIG. 3(c).

Finite Element Analysis (FEA) may then be optionally applied to the 3D objects 304 to simulate multi physical responses based on user interactions. Each dynamic interaction is modelled to reflect the timed interaction of the user with the target AR imagery to be projected in the user view. In the case of a surgical technique, such as a vertical incision, the dynamic interaction is the intersection of the scalpel with the tissue when a vertical cut is made that then leads the tissue to separate.

In some embodiments, commercially-available software packages can be used to slice human anatomy to obtain the layered models 302 shown in FIG. 3(b). These layers are then stitched together in the MRCS environment, resulting in 3D models 304 of vascular and tissue structures, shown in FIG. 3(c), for display and manipulation. In other embodiments, other methods of obtaining the required 3D images may be used and such methods are contemplated to be within the scope of the invention.

The overlay of the virtual models is done within an AR device 210, preferably a head-mounted display (HMD). Preferably, the HMD is a mixed reality device that can be programmed to project virtual imagery into the user's field-of-view. The HMD preferably has additional capabilities for programming such as tracking hand and eye movements of the user. It can also use a spatial mapping feature on the target area to project updated virtual anatomical imagery to dynamically match the physical interactions of a user and a target 3D printed object.

Figure 4C:
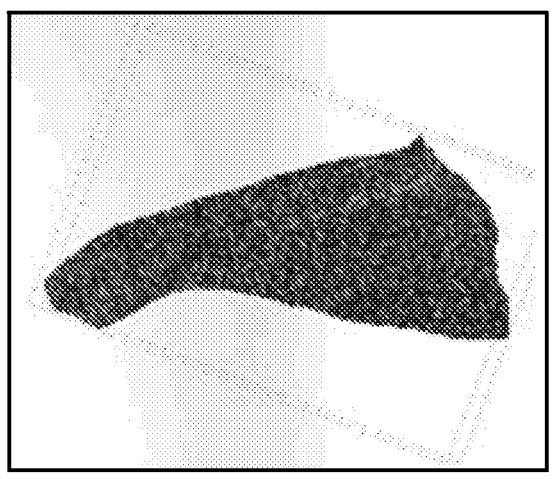
FIG. 4(a) shows 3D imagery of two target tissues.
FIGS. 4(b-c) show STL files of stitched images imagery prior to finite element analysis addition.
Figure 4B:
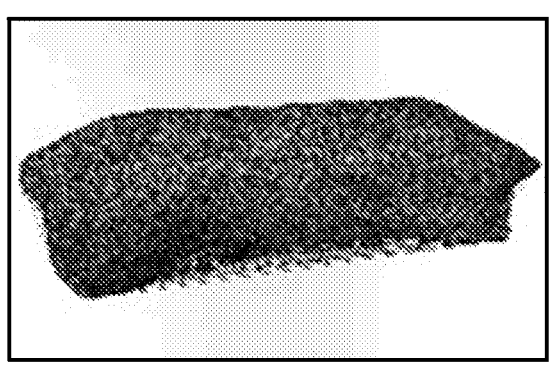
Figure 4A:
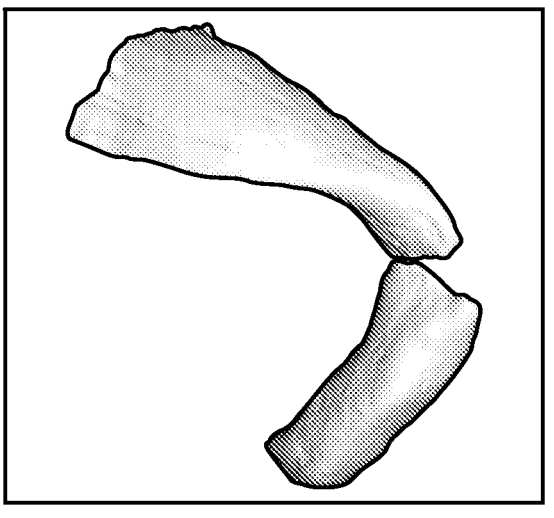

The three-dimensional imagery shown in FIG. 3(c) can be obtained from a composite of 2D images of various objects intended to be in the field-of-view of the user. The process of stitching these 2D images is accomplished, in one embodiment, by fusing multiple 2D images, as shown in FIG. 4(a), which shows 3D imagery of two target tissues. FIGS. 4(b-c) show STL files of the stitched imagery prior to finite element analysis addition.

The final 3D virtual image depends on the target interaction module designed for the user. This allows for multiple iterations and combinations. The 3D imagery can also contain programmed dynamic motions that are triggered by user interaction with the dynamic target in the defined space as monitored by the HMD.

Figures 5A, 5B:
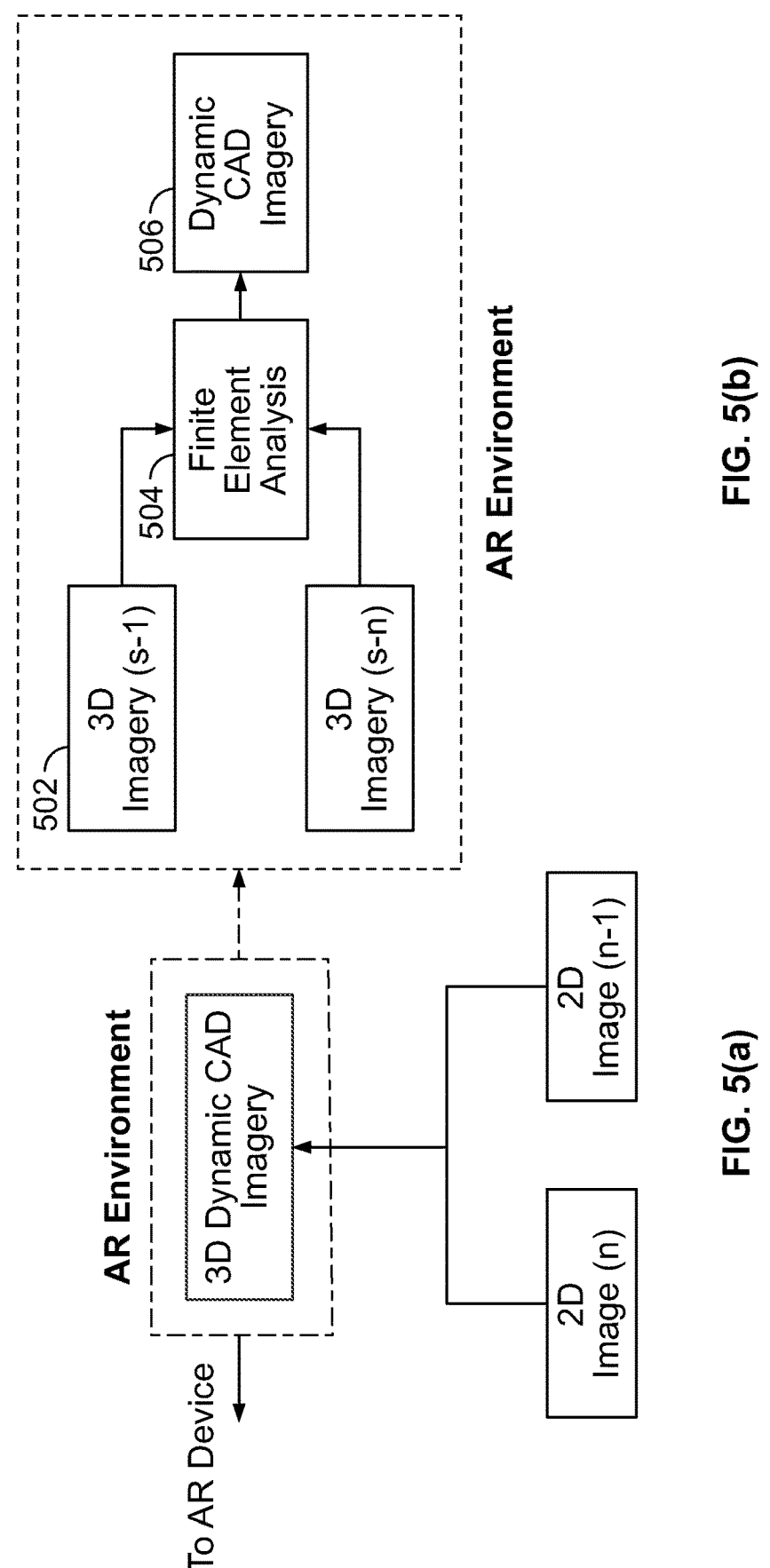
FIG. 5(a) shows the initial 2D image stitching to create the 3D imagery.
FIG. 5(b) shows the addition of the different states of the imagery to create the Dynamic CAD imagery through FEA (finite element analysis)

Multiphysics modeling of dynamic interactions is added to the 3D models 502 using any commercially available finite element modeling software package 504. These dynamic interactions are representations of expected outcomes of the user interactions with the projected AR imagery. FIG. 5 is a schematic diagram showing the finite element analysis. FIG. 5(a) shows 3D imagery generation from stitching, as explained with respect to FIG. 3 and FIG. 4. FIG. 5(b) shows wherein different state positions for the 3D imagery 502 based on finite element analysis 504 are added to provide dynamic 3D imagery 506 for each interaction.

The dynamic responses can be initiated in one of two ways when the AR system recognizes the user in the field. The first way is by having an object boundary for determining the position of the user (or, for example, a surgical instrument) in relation to the projected image and the target object and when the user is in close proximity to the target object. The second instance is by using spatial mapping on the HMD to relate positions of the virtual environment in relation to the physical environment such that the dynamic interaction shown to the user can follow the physical user interactions with the target object.

A virtual environment creator is used to superimpose the dynamic modeling onto the AR imagery. This approach adds dynamic interactions and responses to the projected AR imagery. For this approach, the stitched AR imagery with the finite element analysis module is uploaded to an interactive real-time 3D environment and interaction scripts are either baseline added or manually authored to allow for the desired interaction with the imagery. These scripts can include user interactions such as a manipulation handler for engagement with the projected 3D imagery: an object manipulator to allow for image defined distortion (e.g., during an incision); an elastic manager to recognize different points at which the material properties from the FEA modeling need to match the physical incision act: and a bounds control to pair with the spatial mapping of the HMD to determine where the user and the target object is at any given time.

Figure 6:
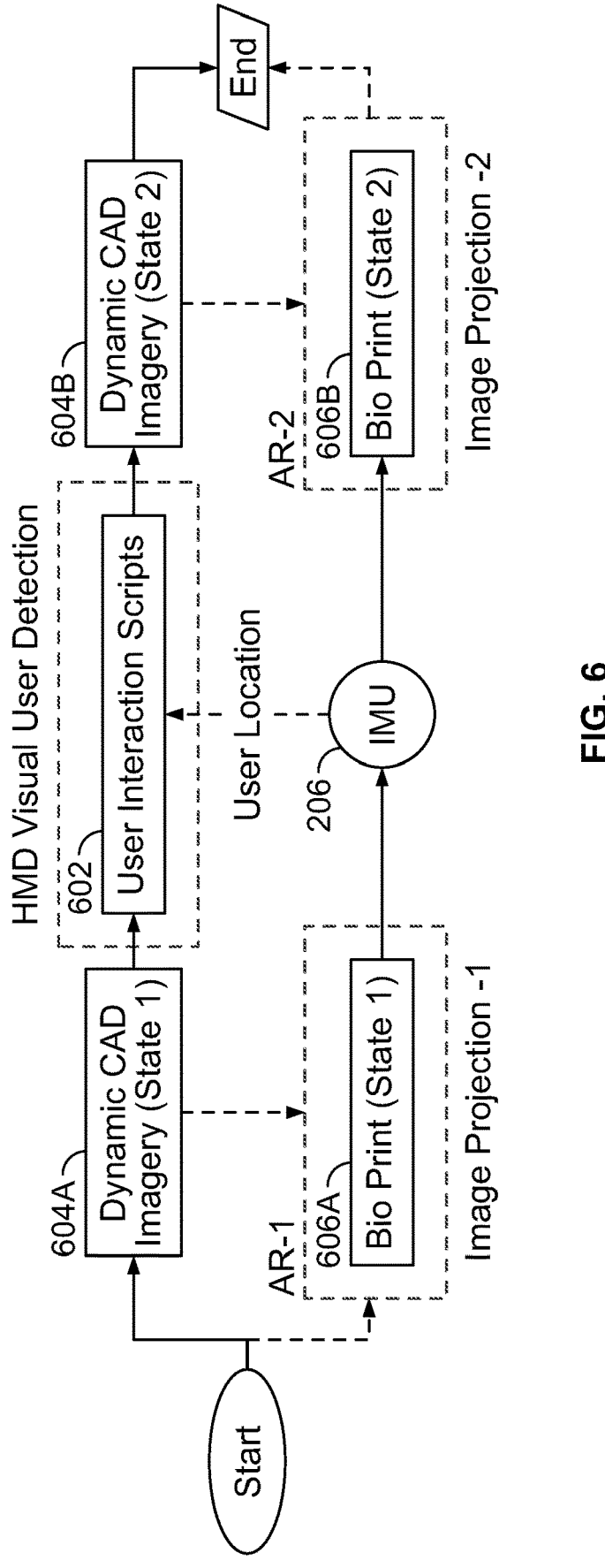
FIG. 6 is a block diagram showing the use of scripts for object interaction in augmented reality (AR) for each group representing either a predicted interaction by the user (image projection) or a user interaction with a bio-specimen.

FIG. 6 shows the use of scripts for object interaction in AR. Each user interaction script 602 represents a predicted interaction by the user and the AR environment that contains the 3D imagery. These scripts are loaded as an application into the AR headset and are used to denote the transition from State 1 604a to State 2 604b of the dynamic 3D imagery. When a user interacts with the 3D printed object, thereby changing it from State 1 606a to State 2 606b, the IMU 206 tracks the user and relays this as additional information to the user interaction scripts 602. The HMD also visually detects the user interaction based on the proximity to the projected virtual environment (VE) 608. Each 3D dynamic imagery state corresponds to a state of the 3D printed object as a virtual environment 608.

Printed Environment—MRCS 200, in one embodiment, involves a bio specimen that is printed using any commercially-available 3D printer capable of being customized to accept bio-print materials. In one embodiment, the 3D bio-prints use 3-4% alginate in an alginate support material cured for 24 hours to approximate human tissue properties. The 3D printed collagen-based bath material for specimen support is, in one embodiment, approximately 60 μm circular gelatin particles that are suitable for printing features of 50-80 μm from a 140 μm nozzle.

The 3D printed bio specimen is customized to reflect the surgical pathology for which surgical planning is difficult to navigate for a practicing clinician. The virtual environment, which is represented by the dynamic CAD imagery from state 1 604*a* to state 2 604*b*, is customized to add the level of detail usually reserved for actual human anatomy interaction such as vasculature. Collagen, as a material, is chosen for the bio printing of the specimen because it mimics human tissue properties.

It should be noted that other objects besides 3D print bio-specimens may_be used with the invention. For example, a repair of a mechanical part may be simulated using a 3D printed version of the part than can be manipulated by the user.

Figure 7:
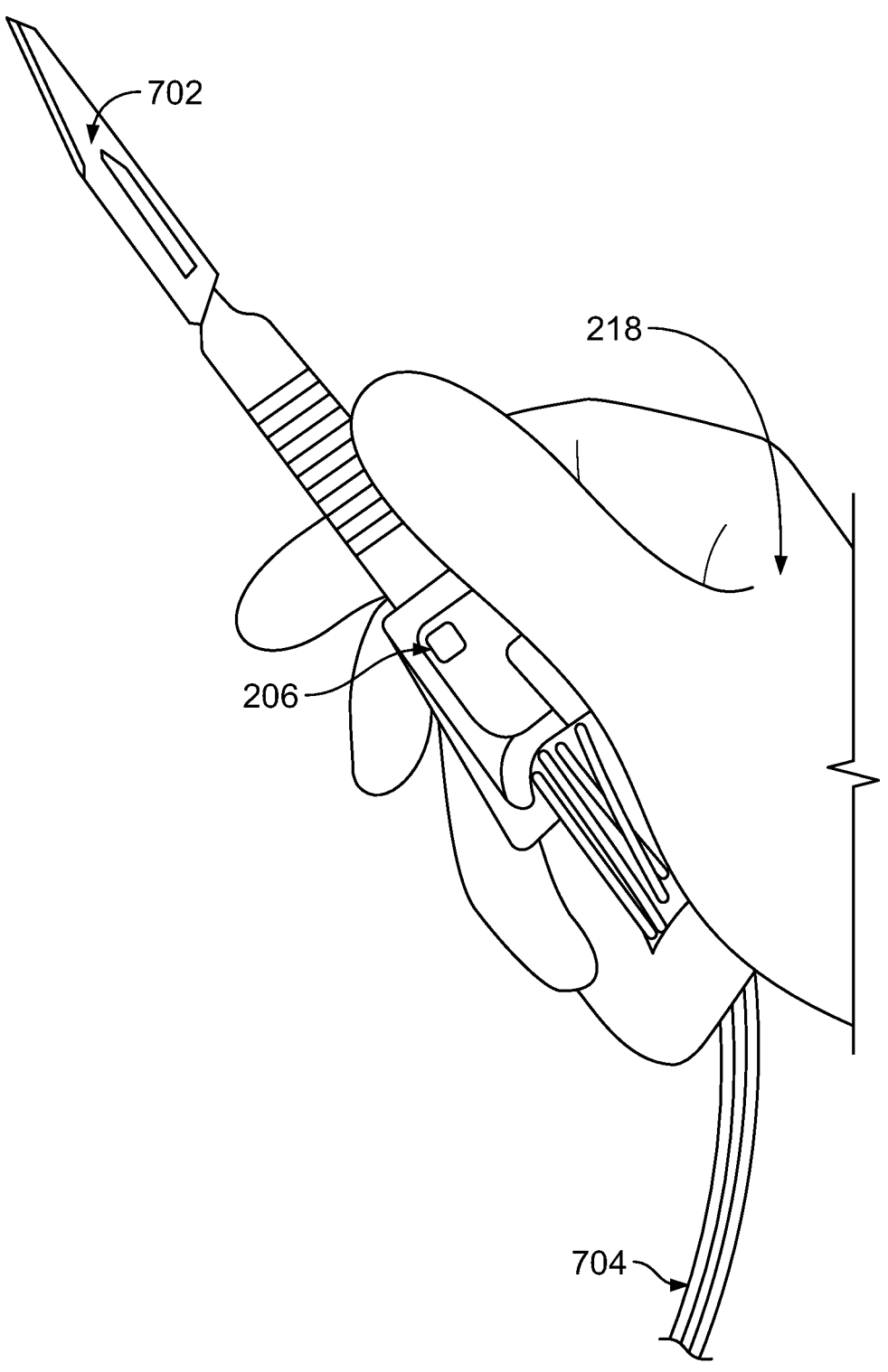
FIG. 7 shows the hand of a user holding a scalpel with the flexible IMU attached thereto as one example of tool that can be used with the disclosed system.
Figure 8A:
FIG. 8 shows a scenario for use with the present invention that overlays on a 3D printed specimen showing a tutorial for a surgical procedure.
Figure 8B:
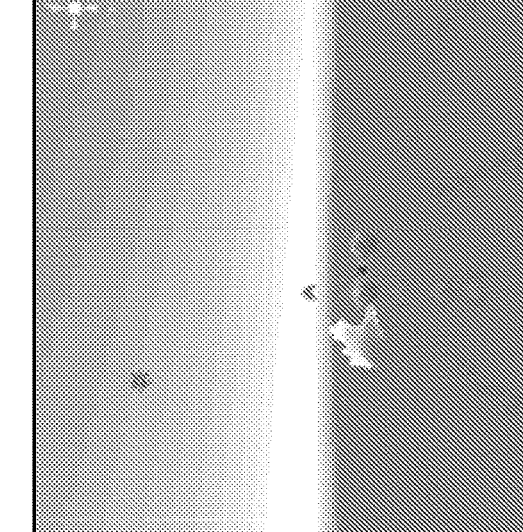
Figure 8C:
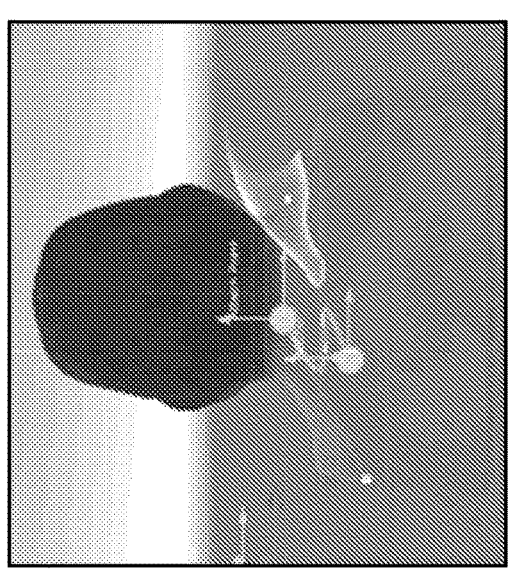
Figure 8D:
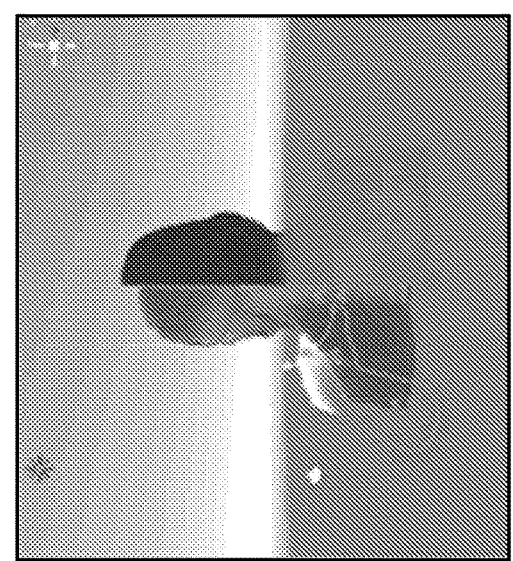

Tracking Environment—The user tracking module consists of two subcomponents. The first is an HMD spatial mapping component for visually tracking the user tools in the field-of-view. The user tool may be, for example, a handheld tool which, in some embodiments, may be a surgical scalpel. The second subcomponent is shown in FIG. 7 and consists of an IMU 206 in the form of a flexible IMU that can be attached to the pivot point of any user tool 702 to track motions of the user 218. Preferably. IMU 206 is a 9 degree-of-freedom IMU, however, any IMU may be used with varying results. In FIG. 7. IMU 206 is shown attached to a surgeon's scalpel 702. The wires 704 attached to flexible IMU 206 are for transmitted signals and are also connected to a power source to power IMU 206. The signals can also be transmitted wirelessly by, for example, via Bluetooth, and, in some embodiments. IMU 206 and related circuitry may be powered by a battery. The user tracking is done to ensure task execution and completion.

To have all three components work, MRCS 200 relies on other sub-architecture components. These are the AR device 210, the user interaction platform and the user interaction module 214

The AR device 210 is a platform with which virtual environments are placed in a physical environment through a user defined interface. The AR device 210 used here is a head mounted display (HMD) worn by the user which may, in one embodiment, be a Microsoft HoloLens 2 (MH2), which can stream virtual environments into the visual frame of the user via 3D imagery. The HMD 210 is programmed to use spatial mapping in a software application to identify the position of the dynamic target object and further overlay the virtual environments onto it. FEA, as previously discussed, is used to model the physical motion of the 3D printed object 212 so that this information can be linked to the AR environment for feedback and motion of the projected system.

Once user interaction is detected in the proximity of the virtual environment being projected onto the dynamic target, through spatial mapping of the space around the target object by HMD 210, the dynamic responses from the 3D printed object 212 can be matched with a custom FEA dynamic modeling outcome. This is done through the authored scripting of the HMD application to recognize, through HMD 210, when the set virtual boundary around the physical object is breached due to dynamic motion of the 3D printed bio specimen. This virtual dynamic response is done to match the physical environment feedback. The matching ensures that the virtual environment in the field-of-view of the user changes to a future expected state of the 3D printed bio specimen. The AR device 210 can detect the motions of the target object and match them with the 3D imagery before, during, and after user interaction. This process is based on the customizable FEA dynamic analysis performed to obtain simulated tissue reactions.

The user platform consists of a user 218, the user interaction module 214, and the dynamic target. The user 218 is the intended recipient of the task planning profile and executes the task. The user interaction module 214 is a set of instructions and commands that can inform user 218 of the interactions required during engagement with the MRCS 200. These commands also include visual aids that assist the user in planning a path for task execution. The dynamic target is an object that demonstrates independent motion when there is engagement from the user, such as bio printed tissue 212. During engagement with the target object 212, the user 218 receives the haptic feedback in a closed loop system ensuring that the actions of user 218 and results from the physical interaction are recorded.

The user interaction module 214 consists of a software application. The software application of the user interaction module 214 is the actual task that the user is required to execute.

FIG. 8 shows a scenario for MRCS 200 that overlays on a 3D printed specimen 212. The tutorial shows the user how to place a surgical incision on the back of the neck. As shown in FIG. 8(*a*), using the right hand of the user to match the field-of-view, the user is shown where to identify the location for the surgical incision. FIG. 8(*b*) shows a cursor showing the location underneath the tissue that the user should be targeting. FIG. 8(*c*) shows an incision line, and the direction is overlaid as virtual imagery instructing the user to make an incision in the suggested direction. FIGS. 8(*c-d*) show the incision direction overlaid on the image of the Obliquus Capitis Inferior (FIG. 8(*c*)) and Rectus Capitis Posterior (FIG. 8(*d*)).

Here, the scenario instructs the user on how to make the surgical incision. A series of steps in this process would include identifying the site of the incision followed by the direction of the surgical incision to be made. This portion serves as the navigation. The anatomy models have no dynamic properties as these properties are only mapped onto the target tissue.

The instructions for task path planning for a surgical incision are, in some embodiments, complemented with additional visual aids that instruct the user on how to perform the incision. These instructions are relayed via a user application interface that the user can commence and serve as the navigation portion of the demonstration. As the user engages with the 3D printed collagen-based specimen generating haptic feedback, the depth and the angular motion of the surgical cut is tracked with IMU 206 and the HMD 210.

Figures 9A, 9B, 9C:
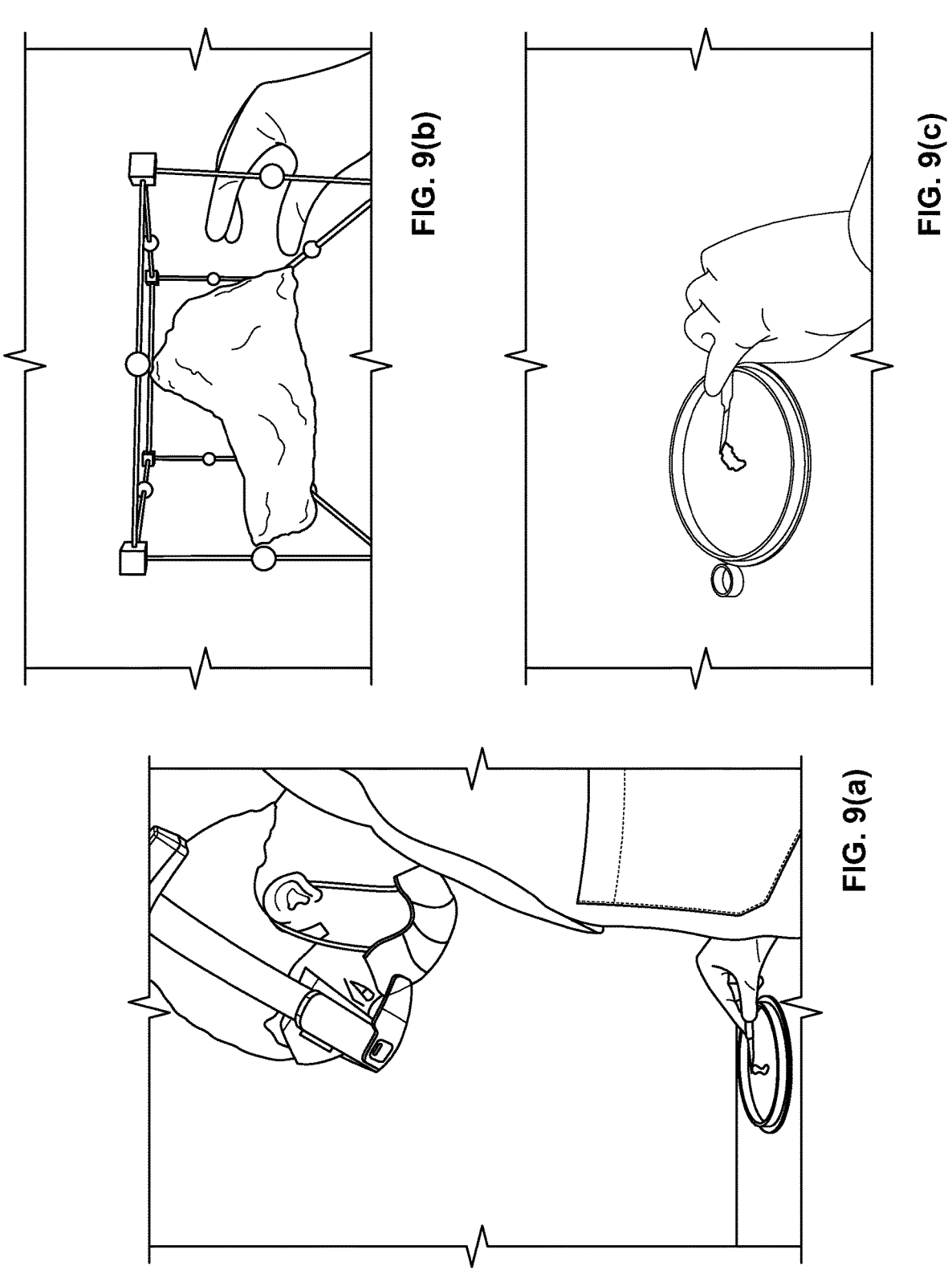
FIGS. 9(a-c) shows several images of a surgical path planning application implemented with the mixed reality combination system disclosed herein.

FIG. 9 shows the user interacting with the MRCS 200. FIG. 9(*a*) shows a user with a HMD making a vertical cut in a bio-printed specimen which corresponds to a pitch (z-axis) absolute angle orientation. FIG. 9(*b*) shows AR imagery in a virtual environment in the user's physical field-of-view. FIG. 9(c) shows an AR environment super-imposed on the 3D bio-printed specimen in the user's field-of-view to track with the incision being made in FIG. 9(a).

This invention provides the ability to not only guide a user's navigation as they are pre-planning a task execution through the image visualization and interaction, but also to track the task execution in achieving task completion. By pairing a 3D printed object and projecting virtual imagery onto it, an augmented reality environment is created for a user that allows them to plan a task prior to execution that is tracked using an IMU.

As would be realized by one of skill in the art, the disclosed method described herein can be implemented by a system comprising a processor and memory, storing software that, when executed by the processor, performs the functions of the system.

As would further be realized by one of skill in the art, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A mixed reality combination system comprising:
an augmented reality environment comprising one or more 3D models of target objects in a target environment;
a printed environment comprising one or more 3D printed objects;
a tracking environment for visually tracking a position and orientation of a tool within the target environment; and
a user interaction module specifying a user task and including visual aids for assisting a user in completion of the specified user task;
wherein the augmented reality environment provides dynamic augmented reality imagery aligned with and projected on the one or more 3D printed objects in a user field-of-view of the target environment in response to motion of a user as tracked by the tracking environment;
wherein the dynamic imagery shows movement of objects in the augmented reality environment in response to the user motions provided by the tracking environment; and
wherein the system predicts a future state of a target object based on the task specified by the user interaction module, manipulates the 3D model representing the target object to show the predicted state and projects imagery showing the predicted state onto the printed environment as the visual aid.

2. The system of claim 1 wherein the augmented reality environment further comprises a virtual environment for superimposing the dynamic 3D imagery onto augmented reality imagery.

3. The system of claim 2 wherein the virtual environment is projected on a heads-up display worn by the user.

4. The system of claim 1 wherein the 3D printed model of an object is a bio specimen composed of collagen to mimic an anatomical structure.

5. The system of claim 4 wherein the mixed reality combination system is used for surgical planning and practice and further wherein the 3D printed bio specimen is customized to reflect a surgical pathology.

6. The system of claim 1 wherein the tracking environment comprises an inertial measurement unit to track movements of the user.

7. The system of claim 6 wherein the inertial measurement unit is integrated with a hand-held tool used by the user to interact with the printed environment.

8. The system of claim 7 wherein the tracking environment further comprises a spatial mapping component to visually track the handheld tool in a field of view of the user.

9. The system of claim 8 wherein the printed environment comprises a bio specimen of an anatomical structure and further wherein the hand-held tool is a scalpel.

10. The system of claim 1 further comprising an augmented reality device which places virtual environments in a physical environment.

11. The system of claim 10 wherein the augmented reality device is a head mounted display worn by the user.

12. The system of claim 1 wherein the dynamic 3D imagery is obtained by:
creating a series of 3D images wherein each 3D image in the series is created by stitching together multiple 2D images;
wherein each 3D image represents a state of an object as the object transitions from the prior state to the next state;
performing finite element modeling to create the dynamic 3D imagery from the series of 3D images.

13. The system of claim 12 wherein the system provides a dynamic response when the user interacts with the virtual environment.

14. The system of claim 13 wherein user interaction with the virtual environment is detected when the position of the user in relation to the printed environment crosses a boundary.

15. The system of claim 13 wherein user interaction with the virtual environment is detected by using spatial mapping to relate positions of the virtual environment in relation to physical movements of the user.

16. The system of claim 1 further comprising:
a processor; and
software, executing on the processor, the software integrating the augmented reality environment, the printed environment and the tracking environment and executing the user interaction module.

17. The system of claim 16 wherein the processor is configured to exchange data with an inertial measurement unit as part of the tracking environment and with a heads-up display as part of the augmented reality environment.

18. A system comprising:
a processor;
a head-mounted display, including a spatial mapping component, in communication with the processor;
one or more tools instrumented with inertial measurement units; and
software that, when executed by the processor, causes the system to:
provide dynamic 3D imagery projected on a 3D printed object in response to motion of a user tracked by the spatial mapping component and the inertial measurement units in the one or more tools.

19. The system of claim 1 wherein finite element analysis is used to simulate multi physical responses of the 3D models to user interactions with the objects.

20. The system of claim 19 wherein the multi physical responses are expected outcomes of user interactions with the projected augmented reality imagery.

21. The system of claim 1 further comprising:

a user interaction platform for detecting user interactions with one of the target objects in a first state and matching dynamic responses from one or more of the 3D printed objects with a custom finite element analysis dynamic modeling outcome of a second state of the target object.

22. The system of claim 1 wherein the system dynamically illustrates a desired user interaction with one or more target objects.

23. The system of claim 22 wherein the illustration of the desired user interaction with one or more target objects remains displayed in the user field-of-view as the user dynamically interacts with the one or more target objects to complete the desired user interaction.

24. The system of claim 1 wherein the one or more 3D models of target objects are created by stitching together multiple layers of 2D images.

25. The system of claim 1 wherein the 3D model of the target object of the task is manipulated to show the predicted state using finite element analysis.

* * * * *